United States Patent [19]
Cortinovis

[11] Patent Number: 6,012,177
[45] Date of Patent: Jan. 11, 2000

[54] THERAPEUTIC SOCK WITH DIFFERENT KNITTED PARTS DUE TO YARN AND ELASTICITY

[75] Inventor: Laura Cortinovis, Collebeato, Italy

[73] Assignee: S.S.I. Sport Socks International S.r.l., Brescia, Italy

[21] Appl. No.: 08/951,274

[22] Filed: Oct. 16, 1997

[51] Int. Cl.[7] .................................................. A41B 11/00
[52] U.S. Cl. ............................................. 2/239; 66/178 A
[58] Field of Search .................................. 2/239, 61, 22, 2/240, 241, 242; 66/178 A, 178 R, 183, 172 E; 602/63, 62

[56] References Cited

U.S. PATENT DOCUMENTS

| | | | |
|---|---|---|---|
| 788,996 | 5/1905 | Bottger, Jr. | 2/239 |
| 1,811,786 | 6/1931 | Frei | 2/239 |
| 2,702,998 | 3/1955 | Purcell | 2/239 |
| 3,975,929 | 8/1976 | Fregeolle | 2/239 |
| 4,172,456 | 10/1979 | Zens | 66/178 A |
| 4,180,065 | 12/1979 | Bowen | 2/239 |
| 4,240,160 | 12/1980 | Imboden et al. | 2/239 |
| 4,253,317 | 3/1981 | Howard et al. | 2/239 |
| 4,397,161 | 8/1983 | Chesebro, Jr. et al. | 2/239 |
| 4,527,402 | 7/1985 | Swallow et al. | 2/239 |

FOREIGN PATENT DOCUMENTS

| | | | |
|---|---|---|---|
| 1224001 | 4/1983 | Canada | 2/239 |

*Primary Examiner*—Amy Vanatta
*Attorney, Agent, or Firm*—McGlew and Tuttle, P.C.

[57] ABSTRACT

A sock for therapeutic use in arterial insufficiency, cardiac and circulatory decompensation, venous insufficiency, arthrosis and rheumatism. The sock includes a leg portion (12), a foot portion (15, 16) and an ankle-neck of the foot portion (12', 14) between the foot and the leg, where at least some of the said portions of the sock have an elasticized knit structure with an elasticity graduated from part to part.

17 Claims, 2 Drawing Sheets

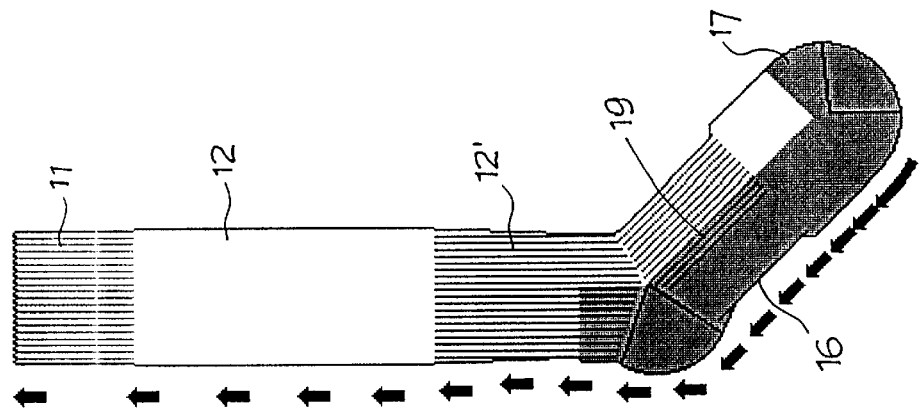
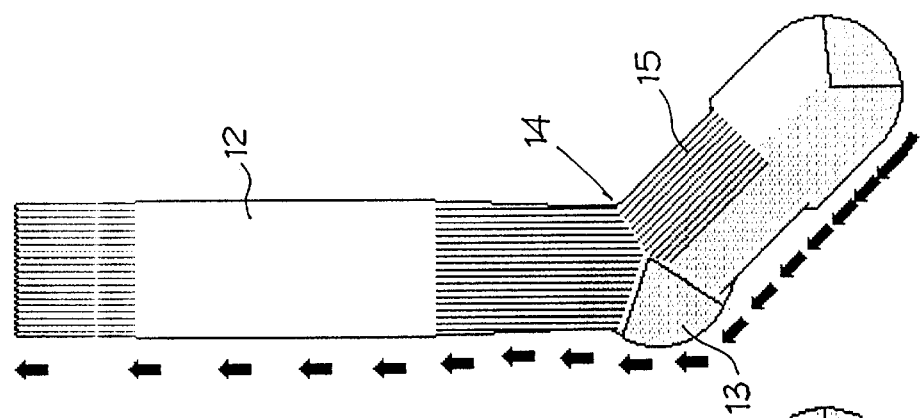
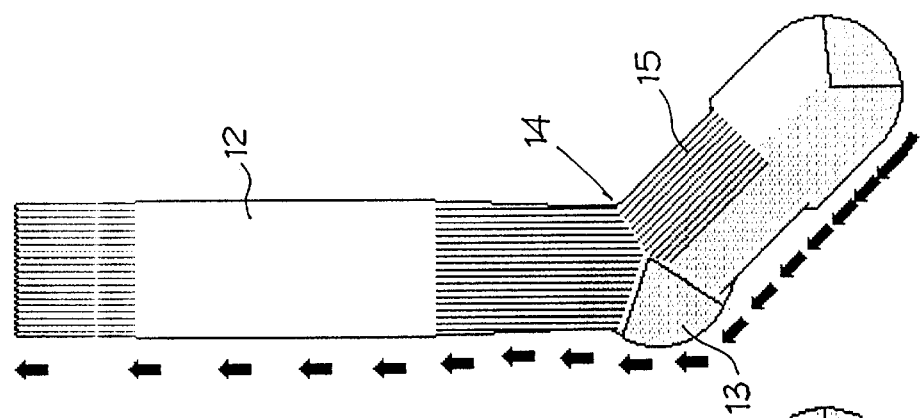
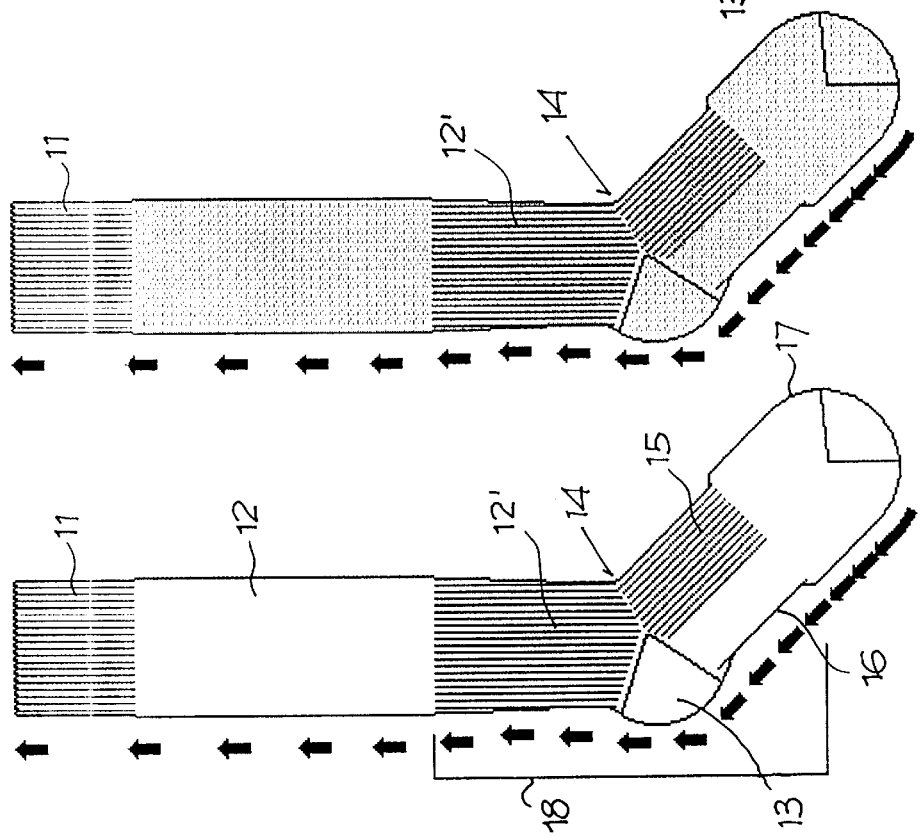

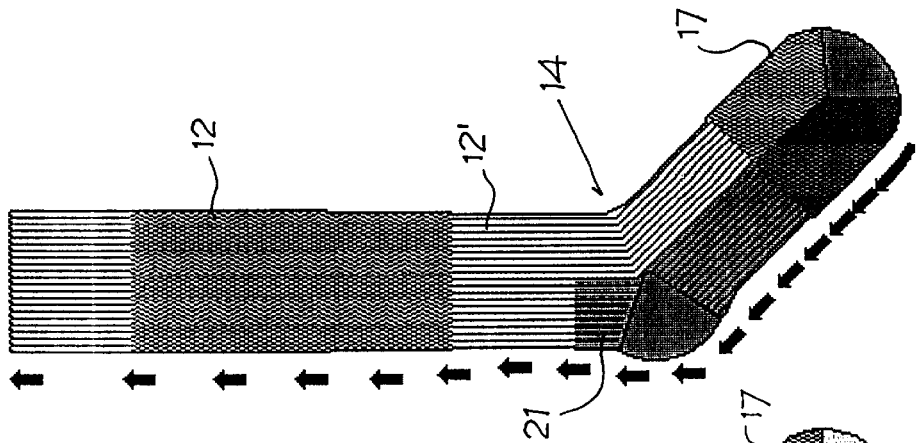
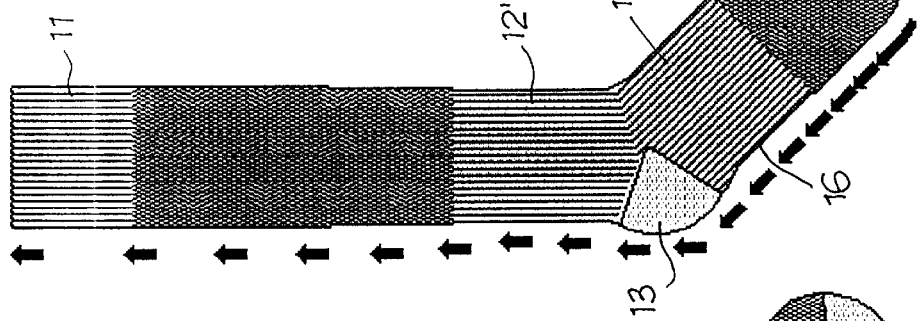
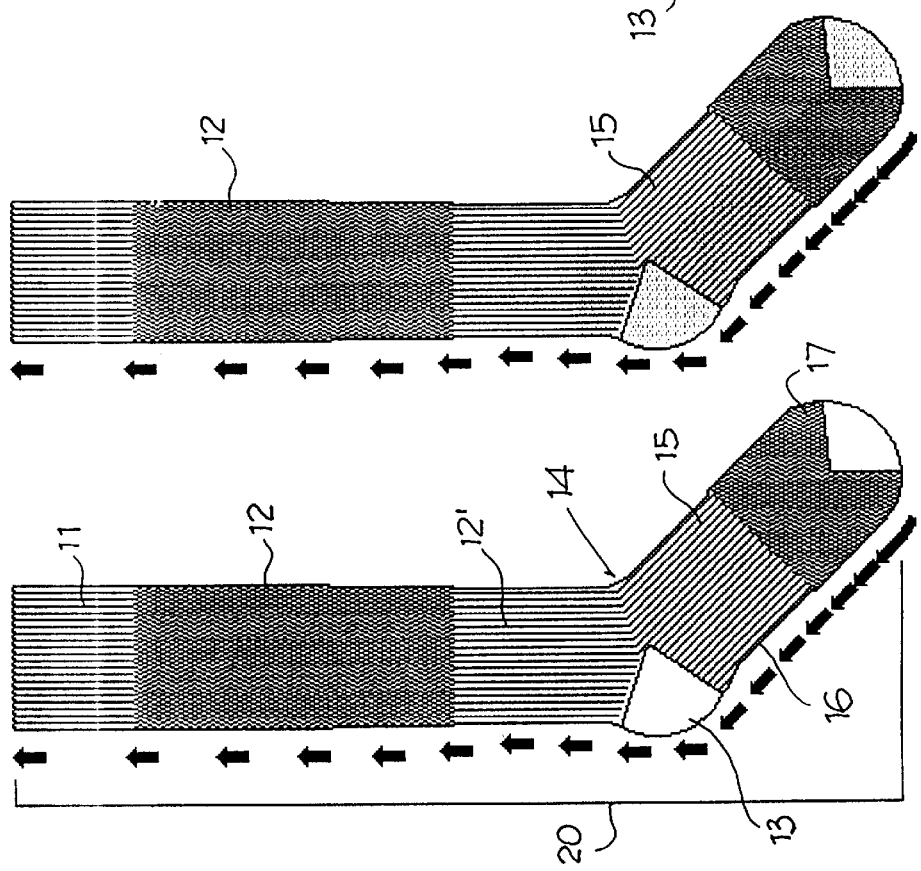

THERAPEUTIC SOCK WITH DIFFERENT KNITTED PARTS DUE TO YARN AND ELASTICITY

FIELD OF THE INVENTION

The present invention concerns the sector of socks, and specifically, it pertains to socks with different knitted parts due to yarn and elasticity for a therapeutic use.

BACKGROUND OF THE INVENTION

Currently, socks are known, which have knitted parts that are different from area to area. However, such socks are used mostly in sports activities. The different parts of the socks are made depending on the sports activity to which the socks are intended and essentially perform the tasks of muscle support, ventilation, and stabilization of specific parts of the foot that are most affected and/or stressed.

SUMMARY AND OBJECTS OF THE INVENTION

On the other hand, the object of the present invention is to provide socks for a health use in the presence, and as an adjuvant in the therapy, of certain diseases, such as arterial insufficiency, cardiac decompensation and circulatory decompensation; venous insufficiency; arthrosis and rheumatism.

Such an object is accomplished by designing the socks so that, besides the maximum wearability, they also perform a mechanical action on the feet, ankles, and legs of the person in response to the movements of the lower limbs, in order to stimulate blood circulation, to compress specific areas as well as to prevent and reduce the feeling of fatigue and swelling of the legs, etc.

Thus, for example, in the presence of arterial insufficiency, and cardiac or circulatory decompensation, the socks act as a pump on the foot and the neck of the foot by stimulating the arterial blood flow; in the presence of venous insufficiency, the socks will build up a diffuse and graduated compression on the entire leg with ascending thrusts to aid venous downflow; for arthrosis and rheumatism, the socks are expected to perform a strong compression and support action at the level of the joints.

The above-mentioned object is accomplished with a sock for therapeutic use comprising a leg portion, a foot portion and an ankle-neck of the foot portion, where at least some of these portions have an elasticized knitted structure with graduated elasticity in order to perform a specific action on the lower limbs of a person.

Greater details of the present invention will become more evident from the description given below with reference to some examples of socks illustrated in the drawings.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 1 is a side view showing a first example of a partially elasticized sock;

FIGS. 2, 3 and 4 are views similar to FIG. 1 showing the embodiment variants of the sock of FIG. 1;

FIG. 5 is a view similar to FIG. 1 showing a second example of a completely elasticized sock; and FIGS. 6, 7 and 8 are views similar to FIG. 1 showing the embodiment variants of the sock of FIG. 5.

DESCRIPTION OF THE PREFERRED EMBODIMENT

Referring to the drawings in particular, a sock according to the invention generally comprises an edge or cuff 11, a leg 12, a heel 13, a part 14 that adapts to the neck of the foot, a part 15 that covers the dorsal aspect of the foot, a sole 16 for the plantar aspect of the foot, and a toe area 17.

The sock is made on a circular stocking knitting machine using prior-art knitting methods available to persons skilled in the art but with an appropriate selection of the yarns and of the type of knitting with which the various parts of the sock are made.

In one embodiment, the sock according to the present invention is made by using at least one basic yarn made of cotton, wool, synthetic, or the like, for the entire sock and one elastic yarn 18, together with the basic yarn, at least in the dorsal area 15 and in the area of the neck of the foot 14 and on a part 12' of the leg 12, at the level of the ankle (see FIG. 1).

The parts of the leg and of the foot, except for the cuff 11, may all be made of smooth jersey as in FIG. 1 or may all be made of terry cloth jersey as in FIG. 2. As an alternative, the foot may have at least the sole 16 made of terry cloth jersey, as shown in FIG. 3. Some parts of the sock may also have reinforcements 19, as shown in FIG. 4, obtained from double terry cloth jersey with the insertion of additional yarns or yarns of varying size, etc.

In the elasticized parts (12', 14, 15) that are obtained with the presence of elastic yarn, the elasticity may be graduated, depending on the therapeutic action that the sock must perform, by varying the percentage of elastomer in the jersey or its size, which will be, e.g., higher in the area of the foot and the ankle and lower in the part 12' of the leg.

The arrows in FIGS. 1 and 4 indicate the "pumping" action of the sock, which tends to aid the circulation of the blood with a venous downflow.

In another embodiment (cf. FIGS. 5, 8) the sock of the present invention is made by using at least one basic yarn made of cotton, wool, synthetic, or the like together with an elastic yarn 20 for the entire sock. Knitted toes of any type may be chosen. Here also, the parts of the foot, the neck of the foot, and the leg may all be made of smooth jersey (cf. FIG. 5), or they may all be made of terry cloth jersey (cf. FIG. 6). As an alternative, the foot may have at least the sole 16 made of terry cloth jersey as shown in FIG. 7. Some parts of the sock may also have reinforced areas 21, as shown in FIG. 8, obtained with a double terry cloth jersey or with additional yarns or yarns of varying size.

This sock, besides by the elastic yarn in all its parts, is characterized in that it has a tighter knit, obtained, i.e., with greater pressure, at least in a part of the foot 15 and of the sole 16, of the neck of the foot 14 and of the leg, especially at the ankle.

Thus, the sock has an elastic structure that is varied from part to part. The knit at the leg 12 and in the toe area 17 of the foot, though elastic, shall be suitable for ventilation, e.g., 1:1 at seams. In the foot/ankle parts, it shall be at the largest seams in order to increase the pressure on the limb and to act as a pump to stimulate the blood circulation.

Moreover, the elasticity may be graduated by using, in the various parts of the sock, yarns having a varying percentage of elastomer varying a knotting of knit curls or yarns of varying denier, therefore maintaining a higher elasticity in the foot/ankle areas and a lower elasticity in the leg.

While specific embodiments of the invention have been shown and described in detail to illustrate the application of the principles of the invention, it will be understood that the invention may be embodied otherwise without departing from such principles.

What is claimed is:

1. A sock for therapeutic use, comprising:

a leg portion;

a foot portion; and an ankle-neck of the foot portion between the foot portion and the leg portion, at least some of said portions of said sock have an elasticized knit structure with an elasticity graduated from portion to portion by a plurality of different elastic yarns, all or parts of the sock being made of smooth jersey.

2. The sock in accordance with claim 1, wherein said leg portion, said foot portion and said ankle-neck of the foot portion all have a knit structure with graduated elasticity from portion to portion.

3. The sock in accordance with claim 1, wherein said leg portion, said foot portion and said ankle-neck of the foot portion all have a knit structure with graduated elasticity.

4. The sock in accordance with claim 1, wherein said portions are formed with at least one basic yarn made of natural or synthetic fibers in all its parts and said elastic yarns together with said basic yarn in the said portions with graduated elasticity.

5. The sock in accordance with claim 3, wherein said portions are formed with at least one basic yarn made of natural or synthetic fibers in all its parts and said elastic yarns together with said basic yarn in said portions with graduated elasticity.

6. The sock in accordance with claim 3, wherein said elasticized portions have a graduated elasticity, by varying a percentage of said elastic yarns in the knit and/or a size of the elastic yarns used and/or by knotting knit curls.

7. A sock for therapeutic use, comprising:

a leg portion;

a foot portion; and an ankle-neck of the foot portion between the foot portion and the leg portion, at least some of said portions of said sock have an elasticized knit structure with an elasticity graduated from portion to portion by a plurality of different elastic yarns;

all or parts of the sock being made of terry cloth jersey.

8. A sock for therapeutic use, comprising:

a leg portion;

a foot portion; and an ankle-neck of the foot portion between the foot portion and the leg portion, at least some of said portions of said sock have an elasticized knit structure with an elasticity graduated from portion to portion by a plurality of different elastic yarns;

at least a sole of said foot portion being made of terry cloth jersey.

9. The sock in accordance with claim 8, wherein:

said elasticity which is graduated includes said foot portion having a different elasticity as compared with an elasticity of said leg portion and said ankle-neck of the foot portion.

10. The sock in accordance with claim 8, wherein:

said elasticity which is graduated includes said foot portion having an elasticity which is gradually varied.

11. A sock in accordance with claim 8, wherein:

each of said plurality of yarns has a different elasticity.

12. A sock in accordance with claim 8, wherein:

each of said plurality of yarns has a varying percentage of elastomer.

13. A sock in accordance with claim 8, wherein:

said plurality of yarns have a varying denier.

14. A sock in accordance with claim 8, wherein:

said elasticity is varied by degrees.

15. A sock in accordance with claim 8, wherein:

said elasticity creates diffuse and graduated compression in a foot of a user.

16. A sock in accordance with claim 8, wherein:

said elasticity varies substantially continuously from one end of said elasticized knit structure to another end of said elasticized knit structure.

17. A sock in accordance with claim 8, wherein:

each of said plurality of yarns has a different elasticity;

said elasticity varies substantially continuously from one end of said elasticized knit structure to another end of said elasticized knit structure, and creates diffuse and graduated compression in a foot of a user.

* * * * *